(12) United States Patent
Gorman et al.

(10) Patent No.: US 6,623,919 B1
(45) Date of Patent: Sep. 23, 2003

(54) OLIGONUCLEOTIDE PRIMERS FOR EFFICIENT MULTIPLEX DETECTION OF HEPATITIS C VIRUS (HCV) AND HUMAN IMMUNODEFICIENCY VIRUS (HIV) AND METHODS OF USE THEREOF

(75) Inventors: Kevin M. Gorman, Penfield, NY (US); David R. Patterson, San Diego, CA (US); Jeffrey M. Linnen, San Diego, CA (US); Keming Song, Ballwin, MO (US)

(73) Assignee: Ortho-Clinical Diagnostics, INC, Raritan, NJ (US)

( * ) Notice: Subject to any disclaimer, the term of this patent is extended or adjusted under 35 U.S.C. 154(b) by 0 days.

(21) Appl. No.: 09/494,332

(22) Filed: Jan. 28, 2000

Related U.S. Application Data
(60) Provisional application No. 60/118,498, filed on Feb. 3, 1999.

(51) Int. Cl.$^7$ ................................................. C12Q 1/70
(52) U.S. Cl. .............................. 435/5; 435/6; 435/91.1; 435/91.2; 536/23.1; 536/24.3; 536/24.32; 536/24.31
(58) Field of Search .................... 435/5, 6; 536/23.1

(56) References Cited

U.S. PATENT DOCUMENTS

| | | | | |
|---|---|---|---|---|
| 5,322,770 A | | 6/1994 | Gelfand ........................ | 435/6 |
| 5,491,225 A | * | 2/1996 | Picone et al. .................. | 435/6 |
| 5,712,385 A | * | 1/1998 | McDonough et al. ......... | 536/24 |
| 5,846,704 A | * | 12/1998 | Maertens et al. .............. | 435/5 |
| 6,001,558 A | * | 12/1999 | Backus et al. ................. | 435/5 |

FOREIGN PATENT DOCUMENTS

| | | | | |
|---|---|---|---|---|
| EP | 0887427 | 12/1998 | ............ | C12Q/1/70 |
| WO | 93/13224 | 7/1993 | ............ | C12Q/1/68 |

OTHER PUBLICATIONS

Han et al. "Characterization of the terminal regions of HCV RNA" PNAS, VOl 88, p. 1711–1715, Mar. 1991.*
Nedjar et al. "Co-amplification of specific sequences of HCV and HIV-1 genomes by using the polymerase chain reaction assay" J. of Virological Methods, VOl 35, p. 297–304, 1991.*
Ahern, www.thescientist.library.upenn.edu/yr1995/july/tools_950724.htlm, Dec. 22, 1998.*
Blasczyk et al. "Allele-specific PCR amplifiaction of factor V Leiden to identify patients at risk for thromboembolism" Beitrage Zur Infusionstherapie und Transfusionmedizin, Vol 34, p. 236–241, 1997– abstract only.*
Kimpton et al. "Evaluation of an automated DNA profiling system employing multiplex amplification of four terameric STR loci" Int. J. Leg. Med. Vol 106, p. 302–311, 1994.*
Research Genetics, Designer PCR, Nucleic Acids Research, Vol 22, No. 15, Aug. 11, 1994.*
Young, et al., 1993, *J. Clin. Microbiol.* 31(4):882.
Myers et al., 1991, *Biochemistry.* 30(3):7661.
Yoo et al., 1989, *J. Biol. Chem.* 764:17078.
Matteucci et al., 1981, *J. Am. Chem. Soc.* 103:3185.
Bukh J. et al.; "Importance of Primer Selection for the Detection of Hepatitis C Virus RNA With The Polymerase Chain Reaction Assay"; *Proceedings of the National Academy of Scienes of USA, US National Academy of Science, Washington*, vol. 89, 1992, pp. 187–191.
Giachetti C. et al.; "Performance evaluation of a HIV–1/HCV RNA multiplex assay"; *Transfusion*, vol. 38, No. 10Sp, Oct., 1998, p. S261.
Gonzales–Villasenor L.I. et al.; "Multiplex RT–PCR based test for HTLV–I/II, HIV-1, HCV and HBV"; *Clinical Chemistry*, vol. 51, No. 11, 1995, p. 9.
Greenbaum K. et al.; "Analytical sensitivity of TMA HIV–1/HCV assay", *Clinical Chemistry*, vol. 45, No. 11, Nov., 1999, p. 2048.
Karachristos A. et al.; "Detection and analysis of hepatitis C virus by a combined RT–PCR method: variation in the 5' non–coding region of the viral genome"; *Journal of Medical Microbiology*, vol. 42, 1995, pp. 367–371.
McDonough S.H. et al.; "High throughput assay for the simultaneous or separate detection of human immunodeficiency virus (HIV) and hepatitis type C virus (HCV)"; *Infusionstherapie und Transfusionsmedizin*, vol. 25, 1998, pp. 164–169.
Roth W.K. et al.; "Comparison of two quantitative hepatitis C virus reverse transcriptase PCR assays"; *Journal of Clinical Microbiology*, vol. 34, No. 2, Feb., 1996, pp. 261–264.
Wolff C et al.; "Transfusionsassoziierte Risiken: Infektionen und Immunmodulation"; *Transfusionsmedizin* (Sibrowski W et al.–Eds.), 1994.

* cited by examiner

Primary Examiner—Jeffrey Fredman
Assistant Examiner—Jeanine Goldberg
(74) Attorney, Agent, or Firm—Darby & Darby

(57) ABSTRACT

Disclosed herein are methods and kits for the simultaneous detection of hepatitis C virus and human immunodeficiency virus in biological samples from human subjects.

46 Claims, No Drawings

OLIGONUCLEOTIDE PRIMERS FOR EFFICIENT MULTIPLEX DETECTION OF HEPATITIS C VIRUS (HCV) AND HUMAN IMMUNODEFICIENCY VIRUS (HIV) AND METHODS OF USE THEREOF

This application claims benefit, under 35 U.S.C. §119(a) to U.S. Provisional Application Ser. No. 60/118,498 filed on Feb. 3, 1999.

FIELD OF THE INVENTION

The present invention pertains to improved methods for detecting nucleic acid sequences in biological samples, particularly sequences derived from infectious microorganisms.

BACKGROUND OF THE INVENTION

Human Immunodeficiency Virus (HIV) infects millions of individuals world-wide and consequently represents a serious public health concern. Spread of HIV infection via contaminated blood products means that there is a need for screening methods that can detect small amounts of HIV RNA in patient samples. Furthermore, the increasing availability of ameliorative treatments for HIV infection means that early detection of infection in a patient is vital in order to initiate appropriate therapeutic interventions.

Hepatitis C Virus (HCV) is a parenterally transmitted virus responsible for the majority of cases of post-transfusion hepatitis and a substantial portion of sporadic (or community acquired) hepatitis cases worldwide. It is estimated that more than 1% of the world's population is infected with HCV. HCV infection is associated with acute hepatitis, chronic hepatitis, cirrhosis, and subsequent hepatocellular carcinoma.

HCV is currently classified as a separate genus, Hepacivirus, in the family Flaviviridae. Its genome consists of a positive-stranded RNA molecule of about 9,500 nucleotides with a single, large open reading frame (ORF) which encodes a polyprotein precursor of about 3,000 amino acids. The large ORF is preceded by a 5' non-coding (NC) region of about 340 nucleotides, which is the most highly conserved region of the genome. The 5' region of the ORF encodes (in a 5'-to-3' direction) a capsid protein, two envelope glycoproteins (E1 and E2), and a small protein of unknown function (P7). The 3' portion of the ORF encodes nonstructural proteins which include a protease, protease/helicase bi-functional protein, RNA polymerase, and regulatory peptides.

Analysis of HCV coding sequences from around the world has revealed considerable sequence variation among individual viral isolates. Furthermore, analyses of HCV sequences from individual patients have shown that the virus circulates as so-called "quasi-species," which contain related but not identical sequences. The variation that exists among isolates and within individual patients is believed to be the result of the low fidelity of the virally-encoded RNA-dependent RNA polymerase. The degree of genetic variability of HCV has important implications for prevention, diagnosis, and control of infection.

Serodiagnosis of HCV infection is typically determined by commercially available enzyme immuno-assays (EIA) which detect antibodies that bind recombinant HCV proteins or peptides. Positive EIA results can be confirmed by a recombinant immunoblot assay (RIBA), but neither EIA nor RIBA assays distinguish past from present infections. Because of the typically low titer of circulating virus, a direct assay for viral proteins has not been successfully developed. Furthermore, antibody-based assays usually fail to detect HCV infection for 2 to 3 months after exposure.

Thus, there is a need in the art for improved assays that allow for the simultaneous screening of patient samples for both HIV and HCV.

SUMMARY OF THE INVENTION

The present invention provides methods for the simultaneous detection of the presence of Hepatitis C Virus (HCV) RNA and Human Immunodeficiency Virus (HIV) RNA in a biological sample using a multiplex assay.

Thus, in one aspect, the invention is directed to a method for co-detecting Hepatitis C Virus (HCV) RNA and Human Immunodeficiency Virus (HIV) RNA in a biological sample. The method comprises:

(A) performing a reverse transcription reaction using RNA derived from the sample as a template and at least one reverse transcription primer that will prime reverse transcription of DNA from HCV RNA and at least one reverse transcription primer that will prime reverse transcription of DNA from HIV RNA to produce reverse transcription products comprising (a) HCV-specific reverse transcription products, (b) HIV-specific reverse transcription products, or (c) a combination of (a) and (b);

(B) amplifying the reverse-transcription products using one or more pairs of oligonucleotide primers specific for the 5' noncoding region of HCV and one or more pairs of oligonucleotide primers specific for HIV to produce amplification products comprising (a) HCV-specific amplification products, (b) HIV-specific amplification products, or (c) a combination of (a) and (b); where each of the pairs of oligonucleotide primers specific for HCV comprises:

```
         (i)       forward       primer
5'-GGGAGAGCCATAGTGGTCTGCGGAA-3' (C131F25) <SEQ ID NO. 1>, and (ii)      reverse       primer
5'-CGGGGCACTCGCAAGCACCCTATCA-3' (C294R25) <SEQ ID NO. 2>;
``` where each of the pairs of oligonucleotide primers specific for HIV-1 comprises a forward primer with the sequence:
5'-CTGCTTAAGCCTCAATAAAGCTTGCCTTGA-3' (JBLTR4) <SEQ ID NO. 3>, and a reverse primer specific for HIV-1 selected from the group consisting of
(1) 5'-GGGTCTGAGGGATCTCTAGTTACC AGAGT-3' (JBLTR6) <SEQ ID NO. 4>, and
(2) 5'-TGTTCGGGCGCCACTGCTAGAGA-3' (JBLTR8) <SEQ ID NO. 5>, and where each of the pairs of oligonucleotide primers specific for HIV-2 comprises a forward primer with the sequence 5'-GGGAGGTTCTCTCCAGCACTAGCA-3' (2LTRe) <SEQ ID NO. 6>, and a reverse primer specific for HIV-2 with the sequence:

5'-GCGACTAGGAGAGATGGGAACACACA-3' (2LTR-R1) <SEQ ID NO. 7>; and (C) detecting the amplification products, where detection of HCV-specific amplification products indicates the presence of HCV RNA in the sample, detection of HIV-specific amplification products indicates the presence of HIV RNA in the sample, and the detection of HCV-specific amplification products and HIV-specific amplification products indicates the presence of HCV RNA and HIV RNA in the sample.

In a second aspect, the invention is directed to a method for co-amplifying Hepatitis C Virus (HCV) DNA and Human Immunodeficiency Virus (HIV) DNA. The method comprises:

(A) performing a polymerase chain reaction on a DNA sample suspected to contain HCV DNA, HIV DNA, or a combination of HCV DNA and HIV DNA, using one or more pairs of oligonucleotide primers specific for the 5' noncoding region of HCV and one or more pairs of oligonucleotide primers specific for HIV to produce amplification products comprising (a) HCV-specific amplification products, (b) HIV-specific amplification products, or (c) a combination of (a) and (b);

where each of the pairs of oligonucleotide primers specific for HCV comprises:
(i) forward primer 5'-GGGAGAGCCATAGTGGTCTGCGGAA-3' (C131F25) <SEQ ID NO. 1>, and
(ii) reverse primer 5'-CGGGGCACTCGCAAGCACCCTATCA-3' (C294R25) <SEQ ID NO. 2>;

where each of the pairs of oligonucleotide primers specific for HIV-1 comprises a forward primer with the sequence:
5'-CTGCTTAAGCCTCAATAAAGCTTGCCTTGA-3' (JBLTR4) <SEQ ID NO. 3>, and a reverse primer specific for HIV-1 selected from the group consisting of:
(1) 5'-GGGTCTGAGGGATCTCTAGTTACC AGAGT-3' (JBLTR6) <SEQ ID NO. 4>, and
(2) 5'-TGTTCGGGCGCCACTGCTAGAGA-3' (JBLTR8) <SEQ ID NO. 5>, and where each of the pairs of oligonucleotide primers specific for HIV-2 comprises a forward primer with the sequence 5'-GGGAGGTTCTCTCCAGCACTAGCA-3' (2LTRe) <SEQ ID NO. 6>, and a reverse primer specific for HIV-2 with the sequence:
5'-GCGACTAGGAGAGATGGGAACACACA-3' (2LTR-R1) <SEQ ID NO. 7>.

In a third aspect, the invention is directed to a method for co-detecting Hepatitis C Virus (HCV) RNA and Human Immunodeficiency Virus (HIV) RNA in a biological sample. The method comprises:

(A) performing a reverse transcription reaction using RNA derived from the sample and internal positive control (IPC) RNA as a template, at least one reverse transcription primer that will prime reverse transcription of DNA from IPC RNA, at least one reverse transcription primer that will prime reverse transcription of DNA from HCV RNA, and at least one reverse transcription primer that will prime reverse transcription of DNA from HIV RNA, to produce reverse transcription products comprising (a) IPC-specific reverse transcription products and (b) HCV-specific reverse transcription products, (c) HIV-specific reverse transcription products, or (d) a combination of any of the foregoing;

(B) amplifying the reverse-transcription products using one or more pairs of oligonucleotide primers specific for IPC, one or more pairs of oligonucleotide primers specific for the 5' noncoding region of HCV, and one or more pairs of oligonucleotide primers specific for HIV to produce amplification products comprising (a) IPC-specific amplification products (b) IPC-specific amplification products and HCV-specific amplification products, (c) IPC-specific amplification products and HIV-specific amplification products, or (d) a combination of any of the foregoing;

where each of the pairs of oligonucleotide primers specific for IPC comprises:
(i) forward primer 5'-CGCCAGCGTGGACCATCAAGT AGTAA-3' (IPCF1) <SEQ ID NO. 8>, and
(ii) reverse primer 5'-CACGATCCTGGAGCAGACACT GAAGA-3' (IPCR1) <SEQ ID NO. 9>;

where each of the pairs of oligonucleotide primers specific for HCV comprises:
(i) forward primer 5'-GGGAGAGCCATAGTGGTCT GCGGAA-3'(C131F25) <SEQ ID NO. 10>, and
(ii) reverse primer 5'-CGGGGCACTCGCAAGCACC CTATCA-3' (C294R25) <SEQ ID NO. 11>;

where each of the pairs of oligonucleotide primers specific for HIV-1 comprises a forward primer with the sequence:
5'-CTGCTTAAGCCTCAATAAAGCTTGCCTTGA-3' (JBLTR4), <SEQ ID NO. 3> and a reverse primer specific for HIV-1 selected from the group consisting of:
(1) 5'-GGGTCTGAGGGATCTCTAGTTACC AGAGT-3' (JBLTR6) <SEQ ID NO. 4>, and
(2) 5'-TGTTCGGGCGCCACTGCTAGAGA-3' (JBLTR8) <SEQ ID NO. 5>,and where each of the pairs of oligonucleotide primers specific for HIV-2 comprises a forward primer with the sequence 5'-GGGAGGTTCTCTCCAGCACTAGCA-3' (2LTRe) <SEQ ID NO. 6>, and a reverse primer specific for HIV-2 with the sequence:
5'-GCGACTAGGAGAGATGGGAACACACA-3' (2LTR-R1) <SEQ ID NO. 7>; and (C) detecting the amplification products, where detection of IPC-specific amplification products indicates the presence of IPC RNA in the sample, detection of HCV-specific amplification products indicates the presence of HCV RNA in the sample, detection of HIV-specific amplification products indicates the presence of HIV RNA in the sample, and the detection of HCV-specific amplification products and HIV-specific amplification products indicates the presence of HCV RNA and HIV RNA in the sample.

In a fourth aspect, the invention is directed to a method for co-amplifying Internal Positive Control (IPC) DNA, Hepatitis C Virus (HCV) DNA, and Human Immunodeficiency Virus (HIV) DNA. The method comprises:

(A) performing a polymerase chain reaction on a DNA sample suspected to contain IPC DNA, HCV DNA, HIV DNA, or a combination of any of the foregoing, using one or more pairs of oligonucleotide primers specific for IPC, one or more pairs of oligonucleotide primers specific for the 5' noncoding region of HCV, and one or more pairs of oligonucleotide primers specific for HIV to produce amplification products comprising (a) IPC amplification products, (b) HCV-specific amplification products, (c) HIV-specific amplification products, or (d) a combination of any of (a), (b), and (c);

where each of the pairs of oligonucleotide primers specific for IPC comprises:

(i) forward primer
5'-CGCCAGCGTGGACCATCAAGTAGTAA-3' (IPCF1) <SEQ ID NO. 8>, and (ii) reverse primer
5'-CACGATCCTGGAGCAGACACTGAAGA-3' (IPCR1) <SEQ ID NO. 9>;

where each of the pairs of oligonucleotide primers specific for HCV comprises:
(i) forward primer 5'-GGGAGAGCCATAGTGGTCTGCGGAA-3' (C131F25) <SEQ ID NO. 10>, and
(ii) reverse primer 5'-CGGGGCACTCGCAAGCACCCTATCA-3' (C294R25) <SEQ ID NO. 11>;
where each of the pairs of oligonucleotide primers specific for HIV-1 comprises a forward primer with the sequence:
5'-CTGCTTAAGCCTCAATAAAGCTTGCCTTGA-3' (JBLTR4) <SEQ ID NO. 3>, and a reverse primer specific for HIV-1 selected from the group consisting of:
(1) 5'-GGGTCTGAGGGATCTCTAGTTACC AGAGT-3' (JBLTR6) <SEQ ID NO. 4>, and
(2) 5'-TGTTCGGGCGCCACTGCTAGAGA-3' (JBLTR8) <SEQ ID NO. 5>, where each of the pairs of oligonucleotide primers specific for HIV-2 comprises a forward primer with the sequence 5'-GGGAGGTTCTCTCCAGCACTAGCA-3' (2LTRe) <SEQ ID NO. 6>, and a reverse primer specific for HIV-2 with the sequence:
5'-GCGACTAGGAGAGATGGGAACACACA-3' (2LTR-R1) <SEQ ID NO. 7>.

In other aspects of the invention, the reverse transcription reaction is performed using random oligonucleotide primers; alternatively, one or more HCV-specific and one or more HIV-specific reverse transcription primers, i.e., oligonucleotides having sequences that correspond to sequences in HCV or HIV RNA, may be used.

Methods for detection of amplification include, without limitation, (a) electrophoresis and (b) capture of amplification products on a solid support to which IPC-, HCV- or HIV-specific probes are attached followed by quantifying the bound products using a colorimetric assay. Useful IPC-specific capture probes include, without limitation, 5'-CTGCGTTAGACCGAGAACTGTGGATAAAGG-3' <SEQ ID NO. 17>. Useful HCV-specific 5' capture probes include, without limitation, 5'-CCTTTCGCGACCCAACACTACTCGGCT-3' <SEQ ID NO. 12>. Useful HIV-1 specific capture probes include, without limitation, 5'-CAACAGACGGGCACACACTACT-3' <SEQ ID NO. 13> and useful HIV-2 specific capture probes include, without limitation, 5'-CCACGCTTGCTTGCTTAAAGACCTC-3' <SEQ ID NO. 14>.

In another aspect, the invention is directed to a kit for co-detecting HCV RNA and HIV RNA in a biological sample. The kit comprises:

(a) a pair of oligonucleotide primers specific for the 5' noncoding region of HCV comprising:

(i) forward primer
5'-GGGAGAGCCATAGTGGTCTGCGGAA-3' (C131F25) <SEQ ID NO. 1>, and (ii) reverse primer
5'-CGGGGCACTCGCAAGCACCCTATCA-3' (C294R25) <SEQ ID NO. 2>;

(b) oligonucleotide primers specific for HIV-1 which comprise a forward primer with the sequence:
5'-CTGCTTAAGCCTCAATAAAGCTTGCCTTGA-3' (JBLTR4) <SEQ ID NO. 3>, and a reverse primer specific for HIV-1 selected from the group consisting of
(1) 5'-GGGTCTGAGGGATCTCTAGTTACC AGAGT-3' (JBLTR6) <SEQ ID NO. 4>, and
(2) 5'-TGTTCGGGCGCCACTGCTAGAGA-3' (JBLTR8) <SEQ ID NO. 5>, and (c) oligonucleotide primers specific for HIV-2 which comprise a forward primer with the sequence 5'-GGGAGGTTCTCTCCAGCACTAGCA-3' (2LTRe) <SEQ ID NO. 6>, and a reverse primer specific for HIV-2 with the sequence:
5'-GCGACTAGGAGAGATGGGAACACACA-3' (2LTR-R1) <SEQ ID NO. 7>.

In yet another aspect, the invention is directed to a kit for co-amplifying HCV DNA and HIV DNA in a DNA sample. The kit comprises:

(a) a pair of oligonucleotide primers specific for the 5' noncoding region of HCV comprising:

(i)   forward   primer
5'-GGGAGAGCCATAGTGGTCTGCGGAA-3' (C131F25) <SEQ ID NO. 1>, and (ii)  reverse   primer
5'-CGGGGCACTCGCAAGCACCCTATCA-3' (C294R25) <SEQ ID NO. 2>;

(b) oligonucleotide primers specific for HIV-1 which comprise a forward primer with the sequence:
5'-CTGCTTAAGCCTCAATAAAGCTTGCCTTGA-3' (JBLTR4) <SEQ ID NO. 3>, and a reverse primer specific for HIV-1 selected from the group consisting of:
(1) 5'-GGGTCTGAGGGATCTCTAGTTACC AGAGT-3' (JBLTR6) <SEQ ID NO. 4>,
(2) 5'-TGTTCGGGCGCCACTGCTAGAGA-3' (JBLTR8) <SEQ ID NO. 5>,and (c) oligonucleotide primers specific for HIV-2 which comprise a forward primer with the sequence 5'-GGGAGGTTCTCTCCAGCACTAGCA-3' (2LTRe) <SEQ ID NO. 6>, and a reverse primer specific for HIV-2 with the sequence:
5'-GCGACTAGGAGAGATGGGAACACACA-3' (2LTR-R1) <SEQ ID NO. 7>.

DETAILED DESCRIPTION OF THE INVENTION

The present inventors have discovered that simultaneous detection of low levels of Hepatitis C Virus (HCV) RNA and Human Immunodeficiency Virus (HIV) RNA in biological samples containing HCV and HIV RNA can be achieved in a multiplex assay by (i) performing a reverse transcription reaction on RNA derived from the sample and (ii) amplifying the reverse transcription products using particular pairs of oligonucleotides having sequences complementary to certain sequences present in HCV and HIV RNA. The present invention thus provides improved single-round, multiplex reverse transcription/amplification assays which detect low copy levels of HCV and HIV RNA in the same samples.

Oligonucleotide primers are selected based on considerations of sequence conservation, intra- and inter-molecular interactions, and the predicted secondary structures of the amplicon and surrounding sequence. Furthermore, the primers and assay system are designed to allow the co-amplification (and co-detection) of multiple regions of the HCV and HIV genomes, multiple viral species, and an internal positive control (IPC) RNA (or DNA). Simultaneous amplification/detection of multiple regions of the viral genomes increases assay sensitivity and the co-amplification of an IPC decreases the likelihood of false negative results because of PCR inhibition.

Many techniques in molecular biology, microbiology, recombinant DNA, and protein biochemistry are used in practicing the present invention, such as those explained in, for example, *Current Protocols in Molecular Biology*, Volumes I, II, and III, 1997 (F. M.. Ausubel ed.); Sambrook et al., 1989, *Molecular Cloning: A Laboratory Manual*, Second Edition, Cold Spring Harbor Laboratory Press, Cold Spring Harbor, New York; *DNA Cloning: A Practical Approach*, Volumes I and II, 1985 (D. N. Glover ed.); *Oligonucleotide Synthesis*, 1984, (M. L. Gait ed.); *Transcription and Translation*, 1984 (Hames and Higgins eds.); *A Practical Guide to Molecular Cloning*, the series, *Methods in Enzymology* (Academic Press, Inc.); and *Protein Purification: Principles and Practice*, Second Edition (Springer-Verlag, N.Y.).

"Nucleic acid" or "polynucleotide" as used herein refers to purine- and pyrimidine-containing polymers of any length, either polyribonucleotides or polydeoxyribonucleotides or mixed polyribo-polydeoxyribo nucleotides. This includes single- and double-stranded molecules, such as, for example, DNA-DNA, DNA-RNA and RNA-RNA hybrids, as well as "protein nucleic acids" (PNA) formed by conjugating bases to an amino acid backbone. This also includes nucleic acids containing modified bases.

A "complement" of a nucleic acid sequence as used herein refers to the antisense sequence that participates in Watson-Crick base-pairing with the original sequence.

A "primer" as used herein is an isolated oligonucleotide between about 5 and about 50 nucleotides in length, preferably between about 6 and about 25 nucleotides in length and most preferably between about 6 and about 18 nucleotides in length, that forms a duplex with a single-stranded nucleic acid sequence of interest and allows polymerization of a complementary strand using, e.g., reverse transcriptase or DNA polymerase.

An "isolated" nucleic acid as used herein refers to a component that is removed from its original environment (for example, its natural environment if it is naturally occurring or a reaction mixture if it is synthetic). An isolated nucleic acid typically contains less than about 50%, preferably less than about 75%, and most preferably less than about 90%, of the components with which it was originally associated.

A nucleic acid sequence that is "derived from" a designated sequence refers to a sequence that corresponds to a region of the designated sequence. This encompasses sequences that are homologous or complementary to the sequence.

An internal positive control (IPC) target nucleic acid refers to a synthetic nucleic acid sequence cloned into a plasmid vector which is subsequently linearized, typically by the action of a restriction endonuclease. An IPC will typically have multiple primer binding sequences surrounding a generic probe-binding region, and acts as a generic control against false negative results in nucleic acid amplification reactions.

The sequence of a preferred internal positive control target DNA is:

5'-CGCCAGCGTGGACCATCAAGTAGTAATGAACGCACGGACGAGGACATCA <SEQ ID NO. 15>.

TAGAGATTACACCTTTATCCACAGTTCTCGGTCTAACGCAGCAGTCAGTG

TATCAGCACCAGCATCCGTAGTGAGTCTTCAGTGTCTGCTCCAGGATCGTG-3'

Nucleic acids comprising any of the sequences disclosed herein or subsequences thereof can be prepared by conventional methods. For example, DNA can be chemically synthesized using, e.g., the phosphoramidite solid support method of Matteucci et al., 1981, *J. Am. Chem. Soc.* 103:3185, the method of Yoo et al., 1989, *J. Biol. Chem.* 764:17078, or other well known methods. The nucleic acids may also be modified by many means known in the art. Non-limiting examples of such modifications include methylation, "caps", substitution of one or more of the naturally occurring nucleotides with an analog, and internucleotide modifications such as, for example, those with uncharged linkages (e.g., methyl phosphonates, phosphotriesters, phosphoroamidates, carbamates, etc.) or charged linkages (e.g., phosphorothioates, phosphorodithioates, etc.). Nucleic acids may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. PNAs are also encompassed by the term "nucleic acid". The nucleic acid may be derivatized by formation of a methyl or ethyl phosphotriester or an alkyl phosphoramidate linkage. Furthermore, the nucleic acid sequences of the present invention may also be modified with a label capable of providing a detectable signal, either directly or indirectly. Exemplary labels include radioisotopes, fluorescent molecules, biotin, and the like.

Amplification as used herein refers to an iterative process by which a nucleic acid is copied. Suitable methods for amplification include without limitation polymerase chain reaction, ligase chain reaction, strand displacement amplification, and nucleic acid single base amplification, and transcription mediated amplification.

The present invention provides methods for detection of HCV and HIV in biological samples. The methods are carried out by
  (i) performing a reverse transcription reaction using as a template RNA contained within or derived from the sample;
  (ii) amplifying the reverse-transcription products, if any, using at least one pair of amplification primers having sequences corresponding to sequences within the genome of HCV, preferably in the 5' noncoding region of HCV, and at least one pair of amplification primers having sequences corresponding to sequences within the genome of HIV, to produce HCV-specific and HIV-specific amplification products; and
  (iii) detecting the HCV-specific and HIV-specific amplification products. Detection of HCV-specific or HIV-specific amplification products indicates the presence of HCV and HIV RNA, respectively, in the sample.

According to the invention, a biological sample is obtained from a patient by any conventional means. Suitable biological samples include, without limitation, blood, serum, plasma, urine, breast milk, and cerebrospinal fluid. Preferably, plasma is used as the source of viral RNA.

The biological sample is treated in any manner that provides access of the reverse transcription reagents to RNA, specifically viral RNA, contained within the sample. RNA "derived from" a biological sample is any RNA which was originally present in the sample and to which access has been gained by treating the sample. Preferably, RNA is extracted from the sample using any method well known in the art, such as, e.g., methods employing guanidinium thiocyanate, or using commercially available reagents and methods such as, e.g., PureScript∂ from Gentra Systems, Inc. (Minneapolis Minn.). Any extraction procedure may be used that results in separation from the RNA of RNases, other proteins, and/or any other components that might interfere with reverse transcription.

The sample is then subjected to reverse transcription using (a) random primers, such as random hexamer primers obtained from Pharmacia Biotech, Piscataway, N.J., and/or (b) primers derived from the 5' or 3' non-coding regions of the HCV RNA genomic sequence. Reverse transcription is carried out using conventional procedures, such as are described in *Current Protocols in Molecular Biology*, Volumes 1, 11, and 111, 1997 (F. M. Ausubel ed.); in U.S. Pat. No. 5,322,770; in Young, et al.,*J. Clin. Microbiol.* 31(4):882 (1993); Myers et al., *Biochemistry* 30(3):7661 (1991); or as described in provisional patent application Ser. No. 60/118, 520, filed Feb. 3, 1999.

Following the reverse transcription reaction, the products are amplified. Any method for amplification may be used, including, without limitation, polymerase chain reaction (PCR), ligase chain reaction, strand displacement reaction, transcription mediated amplification, or nucleic acid single base amplification. Preferably, PCR is used. Typically, a reaction mixture containing all of the necessary components for PCR is added directly to the reverse transcription reaction mixture. Amplification is then carried out using conditions specified by the primer pairs that are used.

The present inventors have discovered certain pairs of HCV-specific and HIV-specific amplification primers may be used simultaneously to detect low levels of both HCV and HIV RNA in patient samples. Non-limiting examples of primers that may be used in practicing the invention include those listed in Table 1 below.

TABLE 1

| ID | Source | Sequence | SEQ ID NO. |
|---|---|---|---|
| JBLTR4 | HIV-1(s) | 5'-CTG CTT AAG CCT CAA TAA AGC TTG CCT TGA-3' | 3 |
| JBLTR6 | HIV-1(as) | 5'-GGG TCT GAG GGA TCT CTA GTT ACC AGA GT-3' | 4 |
| JBLTR8 | HIV-1(as) | 5'-TGT TCG GGC GCC ACT GCT AGA GA-3' | 5 |
| 2LTRe | HIV-2 (s) | 5'-GGG AGG TTC TCT CCA GCA CTA GCA-3' | 6 |
| 2LTR-R1 | HIV-2(as) | 5'-GCG ACT AGG AGA GAT GGG AAC ACA CA-3' | 7 |
| C131F25 | HCV5'(s) | 5'-GGG AGA GCC ATA GTG GTC TGC GGA A-3' | 10 |
| C294R25 | HCV5'(as) | 5'-CGG GGC ACT CGC AAG CAC CCT ATC A-3 | 11 |

(s) = sense strand; (as) = antisense strand

Following amplification, the amplified products may be detected using any method known in the art, including, without limitation, gel electrophoresis in agarose or acrylamide gels; non-isotopic calorimetric detection such as the SureCell® system, available from Ortho Clinical Diagnostics, Rochester, N.Y. (see, e.g., Example 1 below); ECi detection; chemiluminescence, and fluorescence.

The detection of viral-specific amplification products indicates the presence of viral RNA in the sample. When gel electrophoresis is used, viral-specific amplification products are confirmed by their size, as predicted by the location in the respective viral RNA of the sequences corresponding to the amplification primers used in the reaction.

The present invention finds use in the diagnosis of HIV and HCV infection in patients; in testing the efficacy of anti-viral therapeutic regimens; and in screening the blood supply for HCV-infected and HIV-infected samples.

DESCRIPTION OF THE PREFERRED EMBODIMENTS

The following examples illustrate the present invention without limitation.

EXAMPLE 1

Multiplex Detection of HCV and HIV in Biological Samples

The following experiments were performed to determine the sensitivity of multiplex detection of HCV and HIV according to the methods of the present invention.

A. Methods:

1. Patient samples:

Viral loads in HIV positive patient plasma and HCV positive patient plasma were quantified using the Roche Amplicor Assay according to the manufacturer's instructions. HIV-containing and HCV-containing plasma samples were first diluted to contain 1,000 copies/ml and 10,000 copies/ml respectively. They were then combined as follows: To provide 25 copies of viral genomic RNA/PCR reaction, 50 µl of HCV and 500 µl HIV plasma were added to 450 µl negative plasma. To provide 5 copies/PCR reaction, 10 µl of HCV and 100 µl HIV plasma were added to 890 µl negative plasma.

2. Sample preparation:

RNA was prepared from plasma samples using PureScript∂ RNA isolation reagents (Gentra Systems, Minneapolis Minn.). Modifications to the manufacturer's protocol for body fluids included use of 40 µg glycogen, rather than 20 µg, as a carrier to aid in the precipitation of viral RNA. Additionally, in most cases, after isopropyl alcohol precipitation of the RNA and washing the RNA pellet with ethanol, the RNA pellet was resuspended in the RT buffer mix, rather than in the RNA hydration solution provided by the manufacturer.

3. Reverse Transcription:

The synthesis of cDNA from RNA was catalyzed by the addition of 100 U recombinant Moloney Murine Leukemia Virus (M-MLV) reverse transcriptase (RI) (Gibco BRL, Gaithersburg, Md.) in a 50 µl solution of 50 mM Tris-HCl (pH 8.3), 75 mM KCl, 3 mM $MgCl_2$, 10 mM DTT, 0.4 mM of each dNTP (Pharmacia Biotech), 4 µM random hexamers. (Pharmacia Biotech, Piscataway, N.J.) or specific reverse transcription primer, and 20 units RNasin (Promega, Madison, Wis.) in diethylpyrocarbonate (DEPC)-treated water. After incubation at 42° C. for 30 min, the RT reaction was held at 100° C. for 5 min to destroy RT activity. Each reaction was chilled for I min followed by microcentrifugation at 16000×g for 4 seconds.

4. PCR amplification:

PCR was carried out IN A PE9600 thermocycler (Perkin-Elmer) in a 100 µl solution of 25 mM Tris-HCl, 3 mM $MgCl_2$, 0.725 mM EDTA, 54 mM KCl, 3.72 mM NaCl, 40 µM DTT, 108 µg/mL gelatin (type IV), 9.5% glycerol, 0.02% Tween 20, 0.02% NP40, calf thymus DNA (2 µg), 1.2 mM of each dNTP, 0.4 µM of each primer, 10 copies linearized internal positive control (IPC) plasmid DNA, and 16 U of Taq polymerase. Monoclonal antibodies to Taq, TP1-12 and TP4-9, the preparation of which are disclosed in U.S. Pat. No. 5,338,671, were added to the reaction at a 50:1 and 5:1 molar ratio, respectively, to provide a 55:1 molar ratio of antibody to Taq polymerase. After initial denaturation at 96° C. for 3 min, 40 cycles of amplification were performed at 96° C. for 5 sec and 68° C. for 40 sec. At the conclusion of cycling, a post-heat step was performed for 5 min at 103° C. to inactivate Taq polymerase.

5. Detection of PCR products:

PCR products were detected by electrophoresis in 4% agarose gels followed by ethidium bromide staining. Alternatively, PCR products were biotinylated by use of 5'-biotin-labeled primers (sense strand) during amplification. Product was captured by hybridization to oligonucleotide probes covalently attached to latex particles, which were deposited on the surface of a flow through membrane (SureCell® tests . The HIV-1 probes were: 5'-CAACAGACGGGCACACACTACT-3'(JBLTRpr) <SEQ ID NO. 13> and 5'-GAACAGATGGGCACACACTGCT-3'(JBLTRpr4) <SEQ ID NO. 16>; the HIV-2 probe was 5'-CCACGCTTGCTTGCTTAAAGACCTC-3'(2LTRpr1) <SEQ ID NO. 14>; and the HCV probe was 5'-CCT TTC GCG ACC CAA CAC TAC TCG GCT -3' (C252-27P) <SEQ ID NO. 12>. The probe/product complex was reacted with streptavidin (SA)-horseradish peroxidase (HRP) conjugate, which catalyzes the oxidative conversion of a dye precursor to a dye (blue color). The blue color intensity was scored visually (0–10) by comparing color intensity to color standards. All visual color scores >3 were considered to be positive results.

B. Results:

Gel electrophoresis revealed the following amplification products: 188 nt (HCV), 160 nt (IPC), and 150 nt (HIV LTR-long product). The combined HIV and HCV assay was able to detect all combined HIV and HCV samples at 25 copies per PCR test (500 viral particles/ml plasma). In addition, between 50–90% of the combined positive samples were detected at 5 copies/PCR test (100 viral particles/ml plasma). The results are summarized in Table 2, below.

TABLE 2

| # copies viral RNA per PCR reaction. | n = 8 HCV probe positive | n = 8 HIV probe positive |
|---|---|---|
| 0 | 0% | 0% |
| 5 | 88% | 50% |
| 25 | 100% | 100% |

All patents, applications, articles, publications, and test methods mentioned above are hereby incorporated by reference in their entirety.

Many variations of the present invention will suggest themselves to those skilled in the art in light of the above detailed description. Such obvious variations are within the full intended scope of the appended claims.

What is claimed is:

1. A method for detecting Hepatitis C Virus (HCV) RNA or Human Immunodeficiency Virus (HIV) RNA in a biological sample, said method comprising:

(A) performing a reverse transcription reaction using RNA derived from said sample as a template and at least one reverse transcription primer that will prime reverse transcription of DNA from HCV RNA and at least one reverse transcription primer that will prime reverse transcription of DNA from HIV RNA to produce reverse transcription products comprising (a) HCV-specific reverse transcription products, (b) HIV-specific reverse transcription products, or (c) a combination of (a) and (b);

(B) amplifying said reverse-transcription products using one or more pairs of oligonucleotide primers specific for the 5′ noncoding region of HCV and one or more pairs of oligonucleotide primers specific for HIV to produce amplification products comprising (a) HCV-specific amplification products, (b) HIV-specific amplification products, or (c) a combination of (a) and (b);

wherein each of said pairs of oligonucleotide primers specific for HCV comprises:

(i) forward primer 5′-GGGAGAGCCATAGTGGTCTGCGGAA-3′ (C131F25) <SEQ ID NO. 1>, and (ii) reverse primer 5′-CGGGGCACTCGCAAGCACCCTATCA-3′ (C294R25) <SEQ ID NO. 2>;

wherein each of the pairs of oligonucleotide primers specific for HIV-1 comprises a forward primer with the sequence:

5′-CTGCTTAAGCCTCAATAAAGCTTGCCTTGA-3′ (JBLTR4) <SEQ ID NO. 3>, and a reverse primer specific for HIV-1 selected from the group consisting of:

(1) 5′-GGGTCTGAGGGATCTCTAGTTACC AGAGT-3′ (JBLTR6) <SEQ ID NO. 4>, and (2) 5'-TGTTCGGGCGCCACTGCTAGAGA-3' (JBLTR8) <SEQ ID NO. 5>,
wherein each of the pairs of oligonucleotide primers specific for HIV-2 comprises a forward primer with the sequence 5'-GGGAGGTTCTCTCCAGCACTAGCA-3' (2LTRe) <SEQ ID NO. 6>, and a reverse primer specific for HIV-2 with the sequence 5'-GCGACTAGGAGAGATGGGAACACACA-3' (2LTR-R1) <SEQ ID NO. 7>; and (C) detecting said amplification products;
wherein detection of HCV-specific amplification products indicates the presence of HCV RNA in said sample, detection of HIV-specific amplification products indicates the presence of HIV RNA in said sample, and the detection of HCV-specific amplification products and HIV-specific amplification products indicates the presence of HCV RNA and HIV RNA in said sample.

2. A method as defined in claim 1, wherein said reverse transcription reaction is performed using random oligonucleotide primers.

3. A method as defined in claim 1, wherein said reverse transcription reaction is performed using one or more oligonucleotide primers having sequences corresponding to sequences in HCV RNA and one or more oligonucleotide primers having sequences corresponding to sequences in HIV RNA.

4. A method as defined in claim 1, wherein said amplifying is performed by a method selected from the group consisting of polymerase chain reaction, ligase chain reaction, strand displacement amplification, nucleic acid single base amplification, and transcription mediated amplification.

5. A method as defined in claim 1, wherein said detecting comprises visualizing said amplification products by gel electrophoresis.

6. A method as defined in claim 1, wherein said detecting comprises capturing said amplification products on a solid support containing (a) one or more HCV-specific oligonucleotide probes, (b) one or more HIV-specific oligonucleotide probes, or (c) a combination of (a) and (b) and quantifying said captured products using a colorimetric assay.

7. A method as defined in claim 6, wherein said HCV-specific probe consists of 5'-CCTTTCGCGACCCAACACTACTCGGCT-3' (C252-27-PRB) <SEQ ID NO. 12> and said HIV-specific probe is selected from the group consisting of:
(a) 5'-CAACAGACGGGCACACACTACT-3' (JBLTRpr3) <SEQ ID NO. 13>;
(b) 5'-GAACAGATGGGCACACACTGCT-3' (JBLTRpr4) <SEQ ID NO. 16>; and
(c) 5'-CCACGCTTGCTTGCTTAAAGACCTC-3' (2LTRpr1) <SEQ ID NO. 14>.

8. A method as defined in claim 1, wherein said sample is selected from the group consisting of blood, serum, plasma, urine, saliva, and cerebrospinal fluid.

9. A method as defined in claim 1, wherein the HCV and HIV RNA are simultaneously co-detected.

10. A method for amplifying Hepatitis C Virus (HCV) DNA or Human Immunodeficiency Virus (HIV) DNA, said method comprising:
(A) performing a polymerase chain reaction on a DNA sample suspected to contain HCV DNA, HIV DNA, or a combination of HCV DNA and HIV DNA, using one or more pairs of olgonucleotide primers specific for the 5' noncoding region of HCV and one or more pairs of oligonucleotide primers specific for HIV to produce amplification products comprising (a) HCV-specific amplification products, (b) HIV-specific amplification products, or (c) a combination of (a) and (b);
wherein each of said pairs of oligonucleotide primers specific for HCV comprises:
(i) forward primer 5'-GGGAGAGCCATAGTGGTCTGCGGAA-3' (C131F25) <SEQ ID NO.1>, and
(ii) reverse primer 5'-CGGGGCACTCGCAAGCACCCTATCA-3' (C294R25) <SEQ ID NO.2>;
wherein each of the pairs of oligonucleotide primers specific for HIV-1 comprises a forward primer with the sequence:
5'-CTGCTTAAGCCTCAATAAAGCTTGCCTTGA-3' (JBLTR4) <SEQ ID NO.3>, and a reverse primer specific for HIV-1 selected from the group consisting of:
(1) 5'-GGGTCTGAGGGATCTCTAGTTACC AGAGT-3' (JBLTR6) <SEQ ID NO. 4>, and
(2) 5'-TGTTCGGGCGCCACTGCTAGAGA-3' (JBLTR8) <SEQ ID NO. 5>; and
wherein each of the pairs of oligonucleotide primers specific for HIV-2 comprises a forward primer with the sequence 5'-GGGAGGTTCTCTCCAGCACTAGCA-3' (2LTRe) <SEQ ID NO.6>, and a reverse primer specific for HIV-2 with the sequence 5'-GCGACTAGGAGAGATGGGAACACACA-3' (2LTR-R1) <SEQ ID NO.7>.

11. A method as defined in claim 10, further comprising:
(B) detecting said amplification products, wherein detection of HCV-specific amplification products indicates the presence of HCV DNA in said sample, detection of HIV-specific amplification products indicates the presence of HIV DNA in said sample, and the detection of HCV-specific amplification products and HIV-specific amplification products indicates the presence of HCV DNA and HIV DNA in said sample.

12. A method as defined in claim 11, wherein said detecting comprises visualizing said amplification products by gel electrophoresis.

13. A method as defined in claim 11, wherein said detecting comprises capturing said amplification products on a solid support containing (a) one or more HCV-specific oligonucleotide probes, (b) one or more HIV-specific oligonucleotide probes, or (c) a combination of (a) and (b) and quantifying said captured products using a calorimetric assay.

14. A method as defined in claim 13, wherein said HCV-specific probe consists of 5'-CCTTTCGCGACCCAACACTACTCGGCT-3'(C252-27-PRB) <SEQ ID NO. 12> and said HIV-specific probe is selected from the group consisting of:
(a) 5'-CMCAGACGGGCACACACTACT-3' (JBLTRpr3) <SEQ ID NO. 13>;
(b) 5'-GAACAGATGGGCACACACTGCT-3' (JBLTRpr4) <SEQ ID NO. 16>; and
(c) 5'-CCACGCTTGCTTGCTTAAAGACCTC-3' (2LTRpr1) <SEQ ID NO.14>.

15. A method as defined in claim 1, wherein said co-amplifying is simultaneous.

16. A method for detecting Hepatitis C Virus (HCV) RNA or Human Immunodeficiency Virus (HIV) RNA in a biological sample, said method comprising:

(A) performing a reverse transcription reaction using RNA derived from said sample and internal positive control (IPC) RNA as a template, at least one reverse transcription primer that will prime reverse transcription of DNA from IPC RNA, at least one reverse transcription primer that will prime reverse transcription of DNA from HCV RNA, and at least one reverse transcription primer that will prime reverse transcription of DNA from HIV RNA to produce reverse transcription products comprising (a) IPC-specific reverse transcription products, (b) HCV-specific reverse transcription products, (c) HIV-specific reverse transcription products, or (d) any combination of any of the foregoing;

(B) amplifying said reverse-transcription products using one or more pairs of oligonucleotide primers specific for IPC, one or more pairs of oligonucleotide primers specific for the 5' noncoding region of HCV, and one or more pairs of oligonucleotide primers specific for HIV to produce amplification products comprising (a) IPC-specific amplification products, (b) IPC-specific amplification products and HCV-specific amplification products, (c) IPC-specific amplification products and HIV-specific amplification products, or (d) a combination of any of the foregoing;

wherein each of said pairs of oligonucleotide primers specific for IPC comprises:
(1) forward primer
5'-CGCCAGCGTGGACCATCAAGTAGTAA-3' (IPCF1) <SEQ ID NO. 8>, and
(2) reverse primer
5'-CACGATCCTGGAGCAGACACTGAAGA-3' (IPCR1) <SEQ ID NO. 9>;
wherein each of said pairs of oligonucleotide primers specific for HCV comprises:
(i) forward primer
5'-GGGAGAGCCATAGTGGTCTGCGGAA-3' (C131F25) <SEQ ID NO. 10>, and
(ii) reverse primer
5'-CGGGGCACTCGCAAGCACCCTATCA-3' (C294R25) <SEQ ID NO. 11 >; and
wherein each of the pairs of oligonucleotide primers specific for HIV-1 comprises a forward primer with the sequence:
5'-CTGCTTAAGCCTCAATAAAGCTTGCCTTGA-3' (JBLTR4) <SEQ ID NO. 3>, and a reverse primer specific for HIV-1 selected from the group consisting of:
(1) 5'-GGGTCTGAGGGATCTCTAGTTACC AGAGT-3' (JBLTR6) <SEQ ID NO. 4>, and
(2) 5'-TGTTCGGGCGCCACTGCTAGAGA-3' (JBLTR8) <SEQ ID NO. 5>,
wherein each of the pairs of oligonucleotide primers specific for HIV-2 comprises a forward primer with the sequence
5'-GGGAGGTTCTCTCCAGCACTAGCA-3' (2LTRe) <SEQ ID NO. 6>, and a reverse primer specific for HIV-2 with the sequence 5'-GCGACTAGGAGAGATGGGAACACACA-3' (2LTR-R1) <SEQ ID NO. 7>; and (C) detecting said amplification products
wherein detection of IPC-specific amplification products indicates the presence of IPC RNA in said sample, detection of HCV-specific amplification products indicates the presence of HCV RNA in said sample, detection of HIV-specific amplification products indicates the presence of HIV RNA in said sample, and the detection of HCV-specific amplification products and HIV-specific amplification products indicates the presence of HCV RNA and HIV RNA in said sample.

17. A method as defined in claim 16, wherein said reverse transcription reaction is performed using random oligonucleotide primers.

18. A method as defined in claim 16, wherein said reverse transcription reaction is performed using one or more oligonucleotide primers having sequences corresponding to sequences in IPC RNA, one or more oligonucleotide primers having sequences corresponding to sequences in HCV RNA and one or more oligonucleotide primers having sequences corresponding to sequences in HIV RNA.

19. A method as defined in claim 16, wherein said amplifying is performed by a method selected from the group consisting of polymerase chain reaction, ligase chain reaction, strand displacement amplification, and transcription mediated amplification.

20. A method as defined in claim 16, wherein said detecting comprises visualizing said amplification products by gel electrophoresis.

21. A method as defined in claim 16, wherein said detecting comprises capturing said amplification products on a solid support containing (a) one or more IPC specific oligonucleotide probes, (b) one or more HCV-specific oligonucleotide probes, (c) one or more HIV-specific oligonucleotide probes, or (d) a combination of any of (a), (b), and (c) and quantifying said captured products using a colorimetric assay.

22. A method as defined in claim 21, wherein said IPC-specific probe consists of 5'-CTGCGTTAGACCGAGAACTGTGGATAAAGG-3' <SEQ ID NO. 17>, said HCV-specific probe consists of 5'-CCTTTCGCGACCCAACACTACTCGGCT-3' (C252-27-PRB) <SEQ ID NO. 12> and said HIV-specific probe is selected from the group consisting of:
(a) 5'-CAACAGACGGGCACACACTACT-3' (JBLTRpr3) <SEQ ID NO. 13>;
(b) 5'-GAACAGATGGGCACACACTGCT-3' (JBLTRpr4) <SEQ ID NO. 16>; and
(c) 5'-CCACGCTTGCTTGCTTAAAGACCTC-3' (2LTRpr1) <SEQ ID NO. 14>.

23. A method as defined in claim 16, wherein said sample is selected from the group consisting of blood, serum, plasma, urine, saliva, and cerebrospinal fluid.

24. A method as defined in claim 16, wherein the HCV and HIV RNA are co-detected simultaneously.

25. A method for amplifying Internal Positive Control (IPC) DNA, Hepatitis C Virus (HCV) DNA, or Human Immunodeficiency Virus (HCV) DNA, said method comprising:
(A) performing a polymerase chain reaction on a DNA sample containing IPC DNA and suspected to contain HCV DNA, HIV DNA, or any combination of any of the foregoing, using one or more pairs of oligonucleotide primers specific for IPC, one or more pairs of oligonucleotide primers specific for the 5' noncoding region of HCV, and one or more pairs of oligonucleotide primers specific for HIV to produce amplification products comprising (a) IPC amplification products, (b) IPC amplification products and HCV-specific amplification products, (c) IPC amplification products and HIV-specific amplification products, or (d) a combination of any of (a), (b), and (c);

wherein each of said pairs of oligonucleotide primers specific for IPC comprises:

(i) forward primer 5'-CGCCAGCGTGGACCATCAAGTAGTAA-3' (IPCF1) <SEQ ID NO. 8>, and (ii) reverse primer 5'-CACGATCCTGGAGCAGACACTGAAGA-3' (IPCR1) <SEQ ID NO. 9>;

wherein each of said pairs of oligonucleotide primers specific for HCV comprises:

(i) forward primer 5'-GGGAGAGCCATAGTGGTCTGCGGAA-3' (C131F25) <SEQ ID NO.10>, and (ii) reverse primer 5'-CGGGGCACTCGCAAGCACCCTATCA-3' (C294R25) <SEQ ID NO.11>; and wherein each of the pairs of oligonucleotide primers specific for HIV-1 comprises a forward primer with the sequence:

5'-CTGCTTAAGCCTCAATAAAGCTTGCCTTGA-3' (JBLTR4) <SEQ ID NO. 3>, and a reverse primer specific for HIV-1 selected from the group consisting of:

(1) 5'-GGGTCTGAGGGATCTCTAGTTACC AGAGT-3' (JBLTR6) <SEQ ID NO. 4>, and (2) 5'-TGTTCGGGCGCCACTGCTAGAGA-3' (JBLTR8) <SEQ ID NO. 5>, wherein each of the pairs of oligonucleotide primers specific for HIV-2 comprises a forward primer with the sequence 5'-GGGAGGTTCTCTCCAGCACTAGCA-3' (2LTRe) <SEQ ID NO. 6>, and a reverse primer specific for HIV-2 with the sequence 5'-GCGACTAGGAGAGATGGGAACACACA-3' (2LTR-R1) <SEQ ID NO. 7>.

26. A method as defined in claim 25, further comprising:

(B) detecting said amplification products, wherein detection of IPC-specific amplification products indicates the presence of IPC DNA in said sample, detection of HCV-specific amplification products indicates the presence of HCV DNA in said sample, detection of HIV-specific amplification products indicates the presence of HIV DNA in said sample, and the detection of HCV-specific amplification products and HIV-specific amplification products indicates the presence of HCV DNA and HIV DNA in said sample.

27. A method as defined in claim 26, wherein said detecting comprises visualizing said amplification products by gel electrophoresis.

28. A method as defined in claim 26, wherein said detecting comprises capturing said amplification products on a solid support containing (a) one or more IPC- specific oligonucleotide probes, (b) one or more HCV-specific oligonucleotide probes, (c) one or more HIV-specific oligonucleotide probes, or (d) any combination of any of the foregoing and quantifying said captured products using a colorimetric assay.

29. A method as defined in claim 28, wherein said IPC-specific probe consists of 5'-CTGCGTTAGACCGAGAACTGTGGATAAAGG-3' <SEQ ID NO. 17>, said HCV-specific probe consists of 5'-CCTTTCGCGACCCAACACTACTCGGCT-3' (C252-27-PRB) <SEQ ID NO. 12> and said HIV-specific probe is selected from the group consisting of:

(a) 5'-CAACAGACGGGCACACACTACT-3' (JBLTRpr3) <SEQ ID NO. 13>;

(b) 5'-GAACAGATGGGCACACACTGCT-3' (JBLTRpr4) <SEQ ID NO. 16>; and (c) 5'-CCACGCTTGCTTGCTTAAGACCTC-3' (2LTRpr1) <SEQ ID NO. 14>.

30. A method as defined in claim 29, wherein said co-amplifying is simultaneous.

31. A kit suitable for co-detecting HCV RNA and HIV RNA in a biological sample, said kit comprising:

(a) a pair of oligonucleotide primers specific for the 5' noncoding region of HCV comprising:

(i) forward primer 5'-GGGAGAGCCATAGTGGTCTGCGGAA-3' (C131F25) <SEQ ID NO. 10>, and (ii) reverse primer 5'-CGGGGCACTCGCAAGCACCCTATCA-3' (C294R25) <SEQ ID NO. 11 >; and (b) oligonucleotide primers specific for HIV-1 which comprise a forward primer with the sequence:

5'-CTGCTTAAGCCTCAATAAAGCTTGCCTGA-3' (JBLTR4) <SEQ ID NO. 3>, and a reverse primer specific for HIV-1 selected from the group consisting of:

(1) 5'-GGGTCTGAGGGATCTCTAGTTACC AGAGT-3' (JBLTR6) <SEQ ID NO. 4>, and (2) 5'-TGTTCGGGCGCCACTGCTAGAGA-3' (JBLTR8) <SEQ ID NO. 5>,and a pair of oligonucleotide primers specific for HIV-2 which comprise a forward primer with the sequence 5'-GGGAGGTTCTCTCCAGCACTAGCA-3' (2LTRe) <SEQ ID NO. 6>, and a reverse primer specific for HIV-2 with the sequence:

5'-GCGACTAGGAGAGATGGGAACACACA-3' (2LTR-R1) <SEQ ID NO. 7>.

32. A kit as defined in claim 31, further comprising a pair of oligonucleotide primers specific for IPC, wherein said pair of oligonucleotide primers specific for IPC comprises forward primer 5'-CGCCAGCGTGGACCATCAAGTAGTAA-3' (IPCF1) <SEQ ID NO. 8> and reverse primer 5'-CACGATCCTGGAGCAGACACTGAAGA-3' (IPCR1) <SEQ ID NO. 9>.

33. A kit as defined in claim 31, further comprising one or more probes.

34. A kit as defined in claim 32, further comprising one or more probes.

35. A kit as defined in claim 33, wherein said probes are selected from the group consisting of 5'-CCTTTCGCGACCCAACACTACTCGGCT-3' (C252-27-PRB) <SEQ ID NO. 12>, 5'-CMCAGACGGGCACACACTACT-3' (JBLTRpr3) <SEQ ID NO. 13>, 5'-GAACAGATGGGCACACACTGCT-3' (JBLTRpr4) <SEQ ID NO. 16>, and 5'-CCACGCTTGCTTGCTTAAAGACCTC-3' (2LTRpr1) <SEQ ID NO. 14>.

36. A kit as defined in claim 34, wherein said IPC-specific probe consists of 5'-CTGCGTTAGACCGAGAACTGTGGATAAAGG-3' (IPC1P) <SEQ ID NO. 17>, said HCV-specific probe consists of 5'-CCTTTCGCGACCCAACACTACTCGGCT-3' (C252-27-PRB) <SEQ ID NO. 12>, and said HIV-specific probe is selected from the group consisting of:

(a) 5'-CAACAGACGGGCACACACTACT-3' (JBLTRpr3) <SEQ ID NO. 13>;

(b) 5'-GAACAGATGGGCACACACTGCT-3' (JBLTRpr4) <SEQ ID NO. 16>; and (c) 5'-CCACGCTTGCTTGCTTAAAGACCTC-3' (2LTRpr1) <SEQ ID NO. 14>.

37. A kit for co-amplifying HCV DNA and HIV DNA in a DNA sample, said kit comprising:
  (a) a pair of oligonucleotide primers specific for the 5' noncoding region of HCV comprising:
    (i) forward primer 5'-GGGAGAGCCATAGTGGTCTGCGGAA-3' (C131F25) <SEQ ID NO. 10>, and
    (ii) reverse primer 5'-CGGGGCACTCGCAAGCACCCTATCA-3' (C294R25) <SEQ ID NO. 11>;
  (b) oligonucleotide primers specific for HIV-1 which comprise a forward primer with the sequence: 5'-CTGCTTAAGCTCAATAAAGCTTGCCTTGA-3' (JBLTR4) <SEQ ID NO. 3>, and a reverse primer specific for HIV-1 selected from the group consisting of:
    (1) 5'-GGGTCTGAGGGATCTCTAGTTACC AGAGT-3' (JBLTR6) <SEQ ID NO. 4>, and
    (2) 5'-TGTTCGGGCGCCACTGCTAGAGA-3' (JBLTR8) <SEQ ID NO. 5>,and a pair of oligonucleotide primers specific for HIV-2 which comprise a forward primer with the sequence 5'-GGGAGGTTCTCTCCAGCACTAGCA-3' (2LTRe) <SEQ ID NO. 6>, and a reverse primer specific for HIV-2 with the sequence: 5'-GCGACTAGGAGAGATGGGAACACACA-3' (2LTR-R1) <SEQ ID NO. 7>.

38. A kit as defined in claim 37, further comprising a pair of oligonucleotide primers specific for IPC, wherein said pair of oligonucleotide primers specific for IPC comprises forward primer 5'-CGCCAGCGTGGACCATCAAGTAGTAA-3' (IPCF1) <SEQ ID NO. 8> and reverse primer 5'-CACGATCCTGGAGCAGACACTGAAGA-3' (IPCR1) <SEQ ID NO. 9>.

39. A kit as defined in claim 37, further comprising one or more probes.

40. A kit as defined in claim 38, further comprising one or more probes.

41. A kit as defined in claim 39, wherein said probes are selected from the group consisting of 5'-CCTTTCGCGACCCAACACTACTCGGCT-3' (C252-27-PRB) <SEQ ID NO. 12>, 5'-CMCAGACGGGCACACACTACT-3' (JBLTRpr3) <SEQ ID NO. 13>, 5'-GAACAGATGGGCACACACTGCT-3' (JBLTRpr4) <SEQ ID NO. 16>, and 5'-CCACGCTTGCTTGCTTAAAGACCTC-3' (2LTRpr1) <SEQ ID NO. 14>.

42. A kit as defined in claim 40, wherein said IPC-specific probe consists of 5'-CTGCGTTAGACCGAGAACTGTGGATAAAGG-3' (IPC1P) <SEQ ID NO. 17>, said HCV-specific probe consists of 5'-CCTTTCGCGACCCAACACTACTCGGCT-3' (C252-27-PRB) <SEQ ID NO. 12>, and said HIV-specific probe is selected from the group consisting of:
  (a) 5'-CMCAGACGGGCACACACTACT-3' (JBLTRpr3) <SEQ ID NO. 13>;
  (b) 5'-GAACAGATGGGCACACACTGCT-3' (JBLTRpr4) <SEQ ID NO. 16>; and
  (c) 5'-CCACGCTTGCTTGCTTAAAGACCTC-3' (2LTRpr1) <SEQ ID NO. 14>.

43. A method according to claim 1 wherein HCV RNA and HIV RNA are co-detected in the sample by detecting:
  (i) HCV-specific amplification products; and
  (ii) HIV-specific amplification products.

44. A method according to claim 10 wherein HCV DNA and HIV DNA are co-amplified.

45. A method according to claim 16, wherein HCV RNA and HIV RNA are co-detected in the sample by detecting:
  (i) HCV-specific amplification products; and
  (ii) HIV-specific amplification products.

46. A method according to claim 25 wherein the IPC DNA, HCV DNA and HIV DNA are co-amplified.

\* \* \* \* \*

SEQUENCE LISTING

<160> NUMBER OF SEQ ID NOS: 17

<210> SEQ ID NO 1
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 1
gggagagcca tagtggtctg cggaa                                            25

<210> SEQ ID NO 2
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 2
cggggcactc gcaagcaccc tatca                                            25

<210> SEQ ID NO 3
<211> LENGTH: 30
<212> TYPE: DNA
<213> ORGANISM: Artificial Sequence
<220> FEATURE:
<223> OTHER INFORMATION: Oligonucleotide primer

<400> SEQUENCE: 3
ctgcttaagc ctcaataaag cttgccttga                                       30

<210> SEQ ID NO 4
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 4
gggtctgagg gatctctagt tacc                                             24

<210> SEQ ID NO 5
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 5
tgttcgggcg ccactgctag aga                                              23

<210> SEQ ID NO 6
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 6
gggaggttct ctccagcact agca                                             24

<210> SEQ ID NO 7
<211> LENGTH: 26

```
<212> TYPE: DNA
<213> ORGANISM: Artificial Sequence
<220> FEATURE:
<223> OTHER INFORMATION: Oligonucleotide primer

<400> SEQUENCE: 7
gcgactagga gagatgggaa cacaca                                              26

<210> SEQ ID NO 8
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 8
cgccagcgtg gaccatcaag tagtaa                                              26

<210> SEQ ID NO 9
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 9
cacgatcctg gagcagacac tgaaga                                              26

<210> SEQ ID NO 10
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 10
gggagagcca tagtggtctg cggaa                                               25

<210> SEQ ID NO 11
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 11
cggggcactc gcaagcaccc tatca                                               25

<210> SEQ ID NO 12
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 12
cctttcgcga cccaacacta ctcggct                                             27

<210> SEQ ID NO 13
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 13
```

```
caacagacgg gcacacacta ct                                          22

<210> SEQ ID NO 14
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 14
ccacgcttgc ttgcttaaag acctc                                       25

<210> SEQ ID NO 15
<211> LENGTH: 150
<212> TYPE: DNA
<213> ORGANISM: Artificial Sequence
<220> FEATURE:
<223> OTHER INFORMATION: target nucleic acid for an internal positive
      control

<400> SEQUENCE: 15
cgccagcgtg gaccatcaag tagtaatgaa cgcacggacg aggacatcat agagattaca    60
cctttatcca cagttctcgg tctaacgcag cagtcagtgt atcagcacca gcatccgtag   120
tgagtcttca gtgtctgctc caggatcgtg                                   150

<210> SEQ ID NO 16
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 16
gaacagatgg gcacacactg ct                                           22

<210> SEQ ID NO 17
<211> LENGTH: 30
<212> TYPE: DNA
<213> ORGANISM: Artificial Sequence
<220> FEATURE:
<223> OTHER INFORMATION: Oligonucleotide primer

<400> SEQUENCE: 17
ctgcgttaga ccgagaactg tggataaagg                                   30
```